(12) United States Patent
Colman et al.

(10) Patent No.: US 9,498,150 B2
(45) Date of Patent: Nov. 22, 2016

(54) BREATH SAMPLING DEVICE

(75) Inventors: Joshua Lewis Colman, Jerusalem (IL); Gershon Levitsky, Jerusalem (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 1592 days.

(21) Appl. No.: 11/990,442

(22) PCT Filed: Aug. 16, 2006

(86) PCT No.: PCT/IL2006/000949
§ 371 (c)(1),
(2), (4) Date: Nov. 25, 2008

(87) PCT Pub. No.: WO2007/020639
PCT Pub. Date: Feb. 22, 2007

(65) Prior Publication Data
US 2009/0137920 A1    May 28, 2009

Related U.S. Application Data

(60) Provisional application No. 60/709,351, filed on Aug. 16, 2005.

(51) Int. Cl.
*A61B 5/08*    (2006.01)
*B65D 81/00*    (2006.01)
*A61B 5/097*    (2006.01)

(52) U.S. Cl.
CPC .................................... *A61B 5/097* (2013.01)

(58) Field of Classification Search
CPC .... A61B 5/097; A61B 5/087; A61B 5/0836; A61B 5/091
USPC .............. 600/529–543; 128/204.22, 912, 128/207.14–207.16
See application file for complete search history.

(56) References Cited

U.S. PATENT DOCUMENTS

| | | | |
|---|---|---|---|
| 3,877,291 A | 4/1975 | Hoppesch et al. | |
| 4,346,584 A | 8/1982 | Boehringer | |
| 4,558,708 A * | 12/1985 | Labuda et al. | ............... 600/532 |
| 4,818,489 A | 4/1989 | Gonner et al. | |
| 5,857,461 A | 1/1999 | Levitsky et al. | |
| 6,488,635 B1 | 12/2002 | Mottram | |
| 6,935,338 B1 * | 8/2005 | Triunfo, Jr. | ............... 128/204.22 |

(Continued)

FOREIGN PATENT DOCUMENTS

EP    0275105 B2    7/1988

OTHER PUBLICATIONS

PCT Search Report of PCT/IL2006/000949.

(Continued)

*Primary Examiner* — Tiffany Weston
(74) *Attorney, Agent, or Firm* — Rodney J. Fuller; Booth Udall Fuller, PLC

(57) ABSTRACT

There is provided a breath sampling tube comprising a deflector adapted to reduce liquid intake into a sampling inlet. There is also provided a breath sampling tube including a deflector adapted to deflect liquid droplets present in breath to reduce liquid at the sampling inlet. There is also provided a breath sampling system including a gas analyzer and a breath sampling tube comprising a deflector adapted to deflect breath to reduce liquid at the sampling inlet. There is also provided a breath sampling system including a gas analyzer and a breath sampling tube comprising a deflector adapted to deflect liquid droplets present in breath to reduce liquid at the sampling inlet.

11 Claims, 3 Drawing Sheets

(56) References Cited

U.S. PATENT DOCUMENTS

| | | | |
|---|---|---|---|
| 2004/0138577 A1* | 7/2004 | Kline | 600/543 |
| 2004/0216745 A1 | 11/2004 | Yuen | |
| 2005/0137491 A1* | 6/2005 | Paz et al. | 600/543 |

OTHER PUBLICATIONS

Supplementary European Search Report for European Patent Application No. EP06766225.4 dated Mar. 12, 2010 (7 sheets).

* cited by examiner

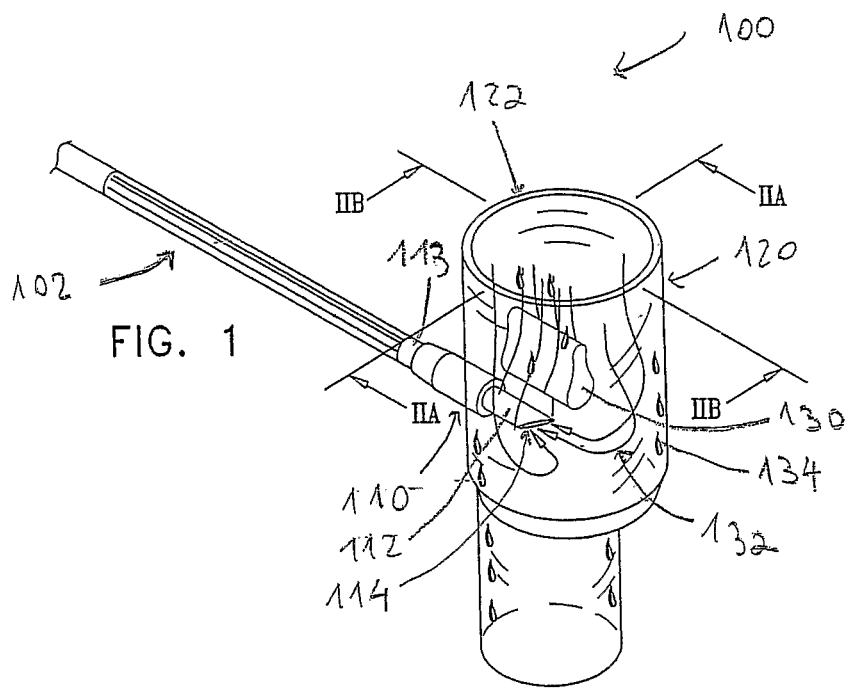
FIG. 1
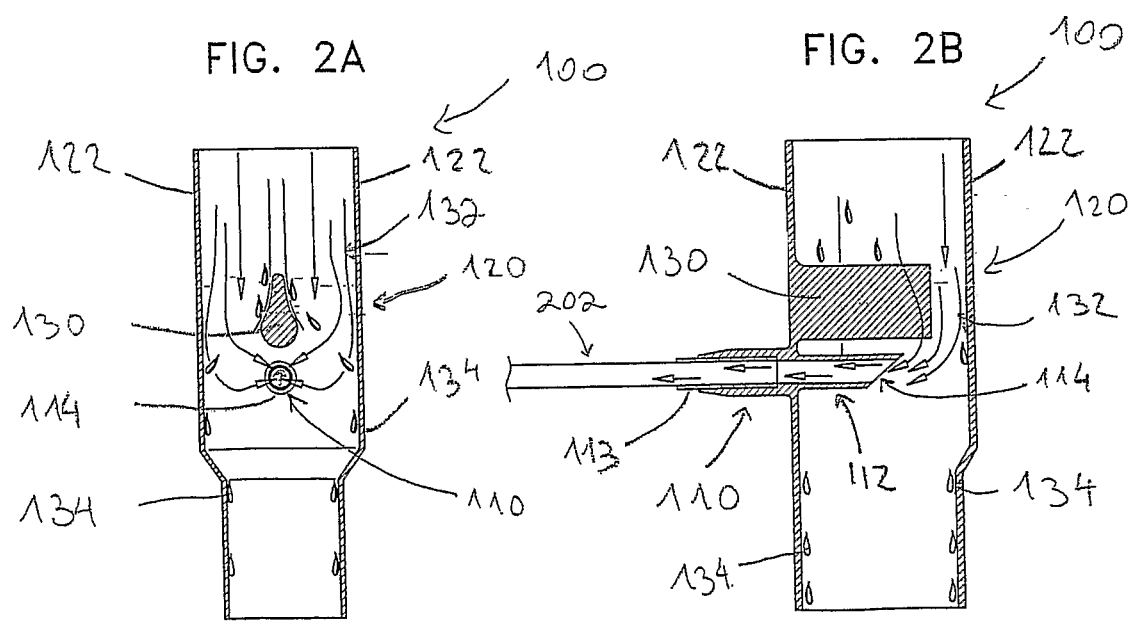
FIG. 2A
FIG. 2B

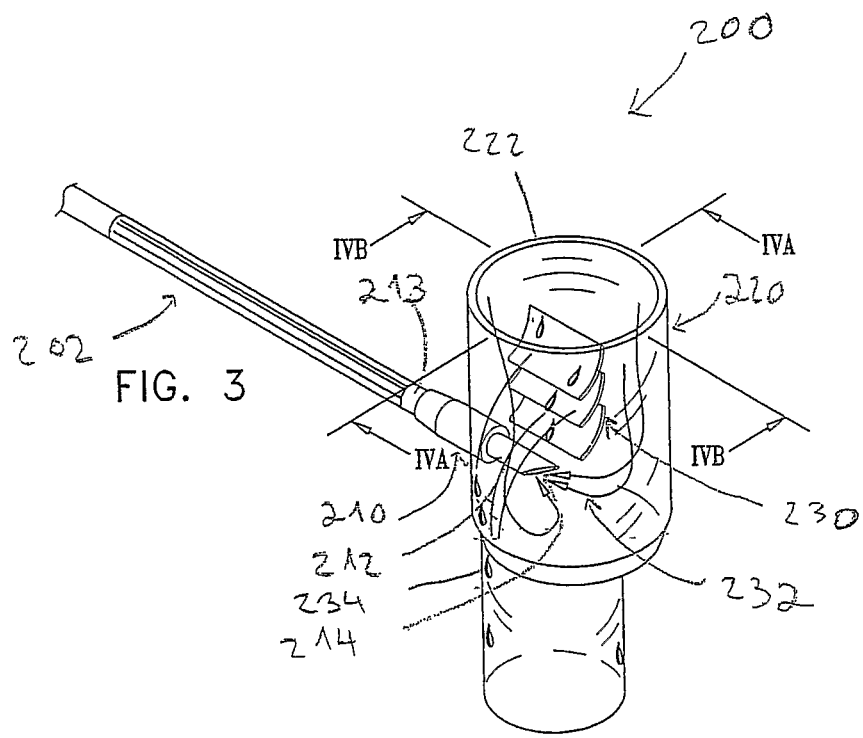
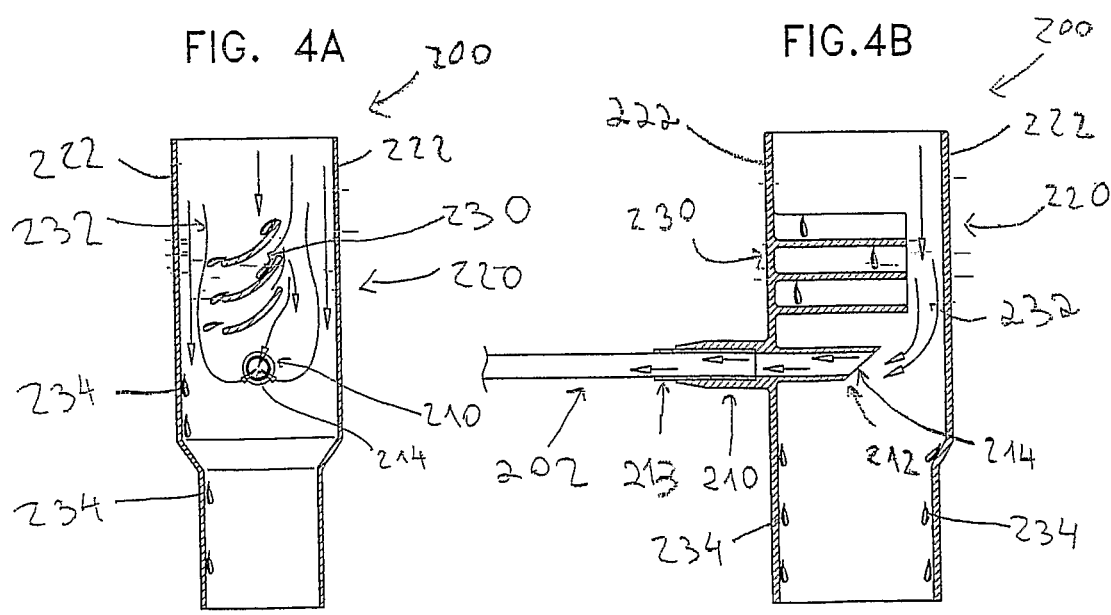

BREATH SAMPLING DEVICE

CROSS-REFERENCE TO RELATED APPLICATIONS

The present application is a US National Phase of PCT Application No. PCT/IL2006/000949, filed on Aug. 16, 2006, which claims the benefit under 35 U.S.C. 119(e) of U.S. Provisional Application 60/709,351 filed Aug. 16, 2005, the entire disclosures of both of which are incorporated herein by reference.

FIELD OF THE DISCLOSURE

The present disclosure relates generally to the field of gas sampling. More particularly, the present disclosure relates to a gas sampling port.

BACKGROUND

Breath gas analysis is commonly performed to provide information related to a patient's condition. An example of a gas analysis often performed is capnography using an analyzer called a capnograph. Capnography is the monitoring of the time dependent respiratory carbon dioxide ($CO_2$) concentration, which may be used to directly monitor the inhaled and exhaled concentration of $CO_2$, and indirectly monitor the $CO_2$ concentration in a patient's blood. Capnography may provide information about $CO_2$ production, pulmonary (lung) perfusion, alveolar ventilation (alveoli are hollow cavities in the lungs in which gas exchange is being performed) and respiratory patterns. Capnography may also provide information related to a patient's condition during anaesthesia, for example by monitoring the concentration of $CO_2$ from anaesthesia breathing circuit and ventilator. More information regarding capnography may be found in http://www.capnography.coin/ and http://www.nda.ox.ac.uk/wfsa/html/u11/u1107_01.htm, which are herein incorporated by reference in its entirety.

In breath analysis systems, for example capnography, breath gas can be sampled either by a mainstream or a sidestream analyzer. In mainstream analyzers the sample chamber is positioned within the patient's gas stream near the patient's end of the breathing system. This arrangement is normally heavier and more cumbersome.

In sidestream analyzers gas is drawn from the breathing system by a tube. The tube, which may be connected to an adaptor near the patient's end of the breathing system, delivers the gas to a sampling place (such as a sampling chamber). There are several elements that are generally common to sidestream breath analysis systems (such as capnographs) including, a monitor that continuously samples and monitors the $CO_2$ in a patients breath, airway tube(s) and sampling line(s) which may be flexible tube(s) having narrower diameter(s) than the airway tube(s), and are adapted used to connect between the patient airway tube(s) and the distant analyzer, such as the capnograph monitor. Along this tube, the patient's breath is continuously sampled.

It is usually preferable that the sampling line is clear of liquids in the fluid sample at all times, in order to permit continuous, non-interfered monitoring. Such liquids are common in patient sampling systems, and have several origins, for example:
  condensed out liquids from the highly humidified air provided to and exhaled from the patient. These liquids typically accumulate both in the patient airway and in the sampling line tubing;
  secretions from the patient, typically found in the patient airway; and
  medications or saline solution provided to the patient during lavage, suction and nebulization procedures.

Condensed out liquids generally refer to water that condenses out from the humidity (the water vapor in a air or in other gas) in the sampling tubes. Condensed out liquids is a major problem commonly hindering breath analyses, particularly sidestream capnography. The internal humidity levels in the tubes are high especially in proximity to the breath collection area since the exhaled and inhaled breath is humid and relatively warm. This is also the case in intubated patients who are generally artificially ventilated with gas (for example, air) having up to 100% humidity at a temperature normally above ambient temperature (for example, about 34° C.), depending on the airway humidification system and patient needs. The humidity (water vapors) often condenses on the tube particularly as the tube is extended farther from the breath collection area due to the temperature decreases.

Several methods have been developed in order to keep the sampling line free of liquids such as those mentioned above, particularly moisture. Some methods are designed to prevent liquids from entering the sampling line (for example, as described in U.S. Pat. No. 5,857,461) and some are designed to remove such liquids if they entered the sampling line or were created in it.

Several solutions have been developed in order to reduce the liquid quantity in the sampling line. Though these solutions have helped in reducing the quantity of low viscosity liquids which enter the sampling line, they have not eliminated the possibility of thick secretions clogging the sampling tubing and its input ports.

Secretions, coughed up by the patient are often thrown at a high speed towards the sampling input ports which are normally positioned at the center of the airway for optimal sampling. Therefore, these sampling ports are often blocked, thereby requiring a user or medical staff to open the patient airway, a condition that one would like to prevent.

There is thus a need to develop methods and apparatuses for reducing the quantity of liquids which reach the sampling line, preferably by preventing liquids from reaching it.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

In some embodiments, there is provided a breath sampling tube including a deflector adapted to reduce liquid intake into a sampling inlet. In other embodiments, there is provided a breath sampling tube including a deflector adapted to deflect liquid droplets present in breath to reduce liquid at the sampling inlet. The deflector is adapted to minimize laminar flow disruption.

In other embodiments, there is provided a breath sampling system including a gas analyzer and a breath sampling tube including a deflector adapted to deflect breath to reduce liquid at the sampling inlet. In other embodiments, there is provided a breath sampling system including a gas analyzer and a breath sampling tube including a deflector adapted to deflect liquid droplets present in breath to reduce liquid at the sampling inlet. The deflector is adapted to minimize laminar flow disruption. The gas analyzer may be a capnograph.

In addition to the exemplary aspects and embodiments described above, further aspects and embodiments will become apparent by reference to the figures and by study of the following detailed descriptions

BRIEF DESCRIPTION OF THE FIGURES

Exemplary embodiments are illustrated in referenced figures. It is intended that the embodiments and figures disclosed herein are to be considered illustrative, rather than restrictive. The disclosure, however, both as to organization and method of operation, together with objects, features, and advantages thereof, may best be understood by reference to the following detailed description when read with the accompanying figures, in which:

FIG. 1 schematically illustrates a sampling system, according to embodiments of the disclosure;

FIG. 2a shows a sectional illustration taken along section line IIA-IIA in FIG. 1;

FIG. 2b shows a sectional illustration taken along section line IIB-IIB in FIG. 1;

FIG. 3 schematically illustrates a sampling system, according to embodiments of the disclosure;

FIG. 4a shows a sectional illustration taken along section line IVA-IVA in FIG. 3;

FIG. 4b shows a sectional illustration taken along section line IVB-IVB in FIG. 3.

Figure 5:
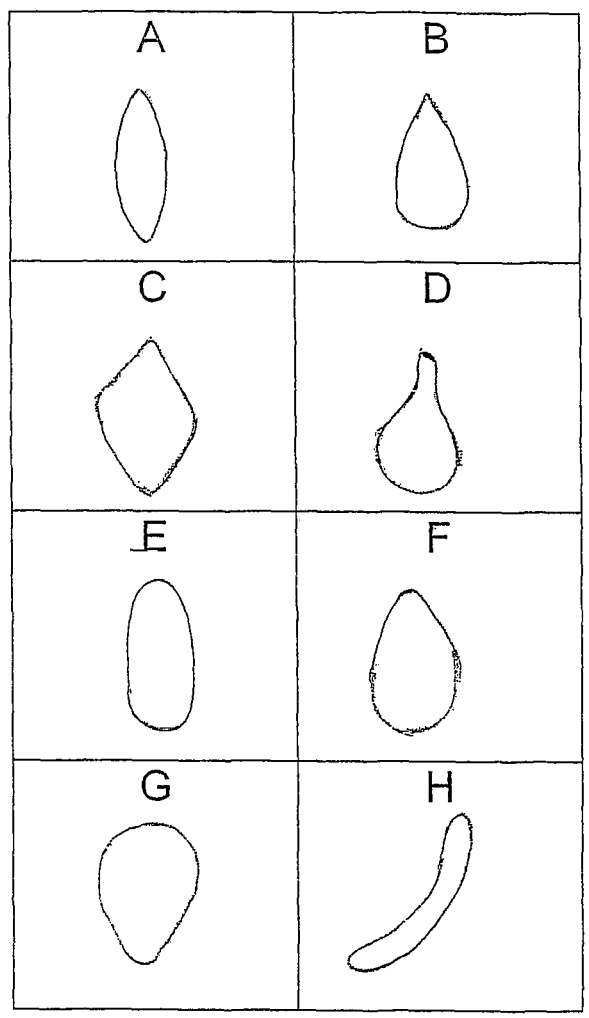
FIG. 5 schematically illustrates exemplary cross section forms of a deflector.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims thereafter introduced be interpreted to include all such modifications, permutations, additions and sub-combinations as are within their true spirit and scope.

In order to solve the problem described hereinabove, and in order to reduce or eliminate the chance that liquids including for example water, secretions, blood, medication saline and the like, will block or clog the sampling tubing input ports, there are provided, according to some embodiments deflector(s) and/or obstacle(s) which are positioned in front of the sampling input port. These deflector(s) which may also be referred to as obstacle(s) may be operative to deflect the liquids or particles containing liquids toward away from the breath sampling inlet(s) for example, towards the walls of an airway adapter.

In some embodiments, there is provided a breath sampling tube including a deflector adapted to reduce liquid intake into a sampling inlet. In other embodiments, there is provided a breath sampling tube including a deflector adapted to deflect liquid droplets present in breath to reduce liquid at the sampling inlet. The deflector is adapted to minimize laminar flow disruption.

In other embodiments, there is provided a breath sampling system including a gas analyzer and a breath sampling tube including a deflector adapted to deflect breath to reduce liquid at the sampling inlet. In other embodiments, there is provided a breath sampling system including a gas analyzer and a breath sampling tube including a deflector adapted to deflect liquid droplets present in breath to reduce liquid at the sampling inlet. The deflector is adapted to minimize laminar flow disruption. The gas analyzer may be a capnograph.

The tube may include an airway adapter, wherein the adapter may include a sampling inlet. In some embodiments, the breath sampling inlet may include opening(s) and/or prong(s) facing towards the inhalation flow direction. In other embodiments, the breath sampling inlet may include opening(s) and/or prong(s) and/or nostril(s) facing towards the exhalation flow direction.

The deflector may be adapted to deflect liquid toward the walls of the airway adapter. The deflector may be located within the airway adapter such that the exhaled breath encounters the deflector prior to reaching the sampling inlet. The deflector may be located essentially in front of the sampling input. The deflector may include one end which is narrower than the opposing end, wherein the narrower end is located farther from the sampling inlet than the opposing end. The deflector may include one end which is narrower than the opposing end, wherein the narrower end is located closer to the sampling inlet than the opposing end.

The cross section of the deflector may be essentially in a shape of a cone, a pear, an ovoid, a lens, a diamond, a rectangular or any combination thereof. The deflector may be formed essentially in a shape of a vane. The deflector may include one or more vanes, for example 2, 3, 4 or 5 vanes or between 5-20 vanes.

The deflector may include a hydrophobic material. The hydrophobic material may prevent or reduce the accumulation of liquids on the deflector.

It is noted that a deflector according to embodiments of this disclosure, may be used in mainstream breath analysis. The deflector may deflect liquids away from the mainstream adapter window(s).

The liquid may include liquid droplet(s), particles including liquid or a combination thereof.

The term "droplet" as referred to herein may include any amount of liquid in any possible shape for example but not limited to, a tear drop or a sphere.

The term "liquid" as referred to herein may include may include any matter a portion of which is not a gas or a solid, for example, water, blood, secretions, medication, saline, suspension colloidal suspension or any combination thereof.

The term "laminar flow" as referred to herein may include a fluid flow which accors in parallel layers, with no disruption between the layers. Reference is now made to FIG. 1, which schematically illustrates an airway adaptor and to FIGS. 2a and 2b, which show sectional illustration taken along section lines IIA-IIA and IIB-IIB, in FIG. 1, respectively. The sampling system 100 is adapted for sampling and analysis of exhaled breath, while reducing the exhaled breath moisture using a moisture reduction system 102 adapted to position a dryer mechanism proximate to a respiratory output device (such as a mask, oral and/or nasal breath collectors, endotracheal tube intubation tube and the like). The sampling system 100 further includes a breath sampling inlet 110. The breath sampling inlet 110 is adapted to connect the moisture reduction system 102 (by the molded-on connector 113) substantially adjacent to the airway adaptor 120 which is adapted to fit into the respiratory output device (particularly, endotracheal tube, intubation tube and the like). FIG. 1 demonstrates a configuration in which the dryer mechanism (particularly, the moisture reduction system 102 is connected directly to the airway adaptor 120. Of course other configurations are possible, for example, where a moisture reduction system, such as the moisture reduction system 102 is connected to an airway adaptor (such as the airway adaptor 120) through tubing (for example, sampling tubes), connector/s (for example, molded-on, non molded-on connectors) grippers (not shown) and the like.

The breath sampling inlet 110 may be integrally formed with the airway adaptor 120 (as shown) or may be attached to the airway adaptor 120. The breath sampling inlet 110 is shown (partially) within an airway adaptor 120. The breath sampling inlet 110 further includes a sampler 112. The sampler 112 includes an opening 114. The sampler 112 may be shaped in any appropriate form and may include sampling prongs which may have a cylindrical form, an open ended box, having a rectangular cross section or any other appropriate form, which are adapted to collect exhaled (and also inhaled) breath (not shown). Of course, sampler 112 may be structured differently, for example in deferent length, position within the airway adaptor 120, angle, number and position of sampling prongs and the like. The sampler 112 may include openings and/or funnel shaped collectors instead of one or more prongs and/or may include, for example one or more (for example 1, 2, 3 or more) prongs in each one of the sampling sides.

The moisture reduction system 102 may include a dryer tube which may include any drying mechanism and/or material that is capable of reducing the moisture level in the sampling system 100 and the sampling tubes. For example, the dryer tube may include Nafion® as referred to herein. In another example, the dryer tube may include filters such as microporous filters or molecular sieves (material containing tiny pores of a precise and uniform size that may be used to absorb moisture). The dryer tube may vary in length and/or in diameter. It is generally preferable that the dryer tube is adapted to absorb moisture and is essentially impermeable to gases. A filter of molecular sieve into which certain materials were impregnates may be included in the drying tube. The moisture reduction system 102 may also include a reinforcing element which is adapted to provide mechanical protection to the drying tube, for example prevent flow interruption, damaging, (partially) blocking, bending and/or collapsing of the drying tube. The reinforcing element may cover a portion of the drying tube. The reinforcing element may include, for example, a braiding net or any other form of mechanical support, such as rigid bars. The sampling tubing may further include another moisture reduction system (not shown), which may be the same or different from moisture reduction system 102 and a coupler that allows the connection of the sampling system 100 to a gas analyzer such as a capnograph (not shown).

The airway adapter 120 includes a deflector 130 located such that at least a part of the exhaled air flow (schematically shown by arrows 132) within the airway adapter 120 will encounter the deflector 130 prior to reaching the sampling inlet 110. As aforementioned, the sampling inlet 110 includes an opening 114 adapted to collect the sampled air. When liquid droplets or particles (depicted as small droplets such as 134), which may be present in an exhaled air flow, encounter the deflector they may be deflected from their initial course to a different course farther from the sampling inlet 110 and thus the amount of liquids that reaches the sampling inlet 110 may be reduced. The deflector 130 may include one end which is narrower than the opposing end, wherein the narrower end may be located farther from the sampling inlet than the opposing end. Alternatively, the narrower end may be located closer to the sampling inlet than the opposing end. Alternatively, both ends may be narrowed.

The deflectors (obstacles), such as deflector 130, may be positioned in front of the sampler 112. These deflectors (obstacles) may be operative to deflect the liquids toward the wall(s) 122 of the airway adapter 120. The liquids and secretions, which have relatively high inertia and which are flying toward the sampler 112, will be deflected to the sides, whereas the air (gas) current circumvents the obstacles and may enter the sampler 112 as required. The characteristics of the deflection of a liquid droplet and/or a particle containing liquid may be affected by various factors and/or causes such as, speed of the liquid droplet and/or the particle containing liquid, the, viscosity and/or direction thereof, material of deflector, air flow speed, pressure of ventilator and other factors.

In one embodiment, the deflector may deflect water droplets of more than 2 microliter. In another embodiment, the deflector may deflect water droplets of more than 5 microliter. In another embodiment, the deflector may deflect water droplets of more than 10 microliter.

In one embodiment, the deflector may deflect droplets and/or particles which include secretions having a volume of more than 0.1 microliter. In another embodiment, the deflector may deflect water droplets of more than 0.2 microliter. In another embodiment, the deflector may deflect water droplets of more than 0.5 microliter.

The cross section of the deflector(s) referred to herein may be essentially in the shape of a cone, a pear, an ovoid, a lens, a diamond, a rectangular or any combination thereof. Although FIGS. 1, 2*a* and 2*b* show a deflector having pear shaped cross section, it is noted that any other appropriate deflector shape (such as but not limited to the examples provided herein) may be applied.

The deflector 130 (or any other appropriate deflector) may be formed with and/or attached to a portion of the wall(s) 122 or the airway adapter 120.

The deflector 130 (or any other appropreate deflector) may refer to a molded-on deflector, which may be a part of (such as an integral part of) the airway adapter 120 (or any other appropreate airway adapter) and/or a separate element.

Deflecting the liquids that may be present in exhaled breath prior to their reaching the sampling inlet and thus preventing/reducing their entrance into the sampling tubes may solve or at least reduce the problem of damages caused by these liquids (for example, blocking and/or clogging the sampling tubing and input ports and damaging the analyzer).

According to some embodiments of the disclosure, one or more deflectors may be positioned such that the exhaled breath flow encounter the deflector(s) (such as deflector 130) prior to reaching the sampling inlet (such as sampling inlet 110). Preferably, the mechanism may be based on aerodynamic principles, such that the essentially laminar gas (breath) flow will be maintained.

For example, since liquids and secretions have higher inertia in comparison to the gas, the deflector(s) (such as deflector 130) may thus deflect the liquids and secretions away from the sampling inlet (such as sampling inlet 110) whereas the air circumvents the deflector(s) and enters the sampling inlet as required.

Reference is now made to FIG. 3, which schematically illustrates an airway adaptor and to FIGS. 4a and 4b, which show sectional illustration taken along section lines IVA-IVA and IVB-IVB, in FIG. 1, respectively. The sampling system 200 is adapted for sampling and analysis of exhaled breath, while reducing the exhaled breath moisture using a moisture reduction system 202 adapted to position a dryer mechanism proximate to a respiratory output device (such as a mask, oral and/or nasal breath collectors, endotracheal tube intubation tube and the like). The sampling system 200 further includes a breath sampling inlet 210. The breath sampling inlet 210 is adapted to connect the moisture reduction system 202 (by the molded-on connector 213) substantially adjacent to the airway adaptor 220 which is adapted to fit into the respiratory output device (particularly, endotracheal tube, intubation tube and the like). FIG. 2 demonstrates a configuration in which the dryer mechanism (particularly, the moisture reduction system 202 is connected directly to the airway adaptor 220. Of course other configurations are possible, for example, where a moisture reduction system, such as the moisture reduction system 202 is connected to an airway adaptor (such as the airway adaptor 220) through tubing (for example, sampling tubes), connector/s (for example, molded-on, non molded-on connectors) grippers (not shown) and the like. The breath sampling inlet 210 may be integrally formed with the airway adaptor 220 (as shown) or may be attached to the airway adaptor 220. The breath sampling inlet 210 is shown (partially) within an airway adaptor 220. The breath sampling inlet 210 further includes a sampler 212. The sampler 212 includes an opening 214. The sampler 212 may be shaped in any appropriate form and may include sampling prongs which may have a cylindrical form, an open ended box, having a rectangular cross section or any other appropriate form, which are adapted to collect exhaled (and also inhaled) breath (not shown). Of course, sampler 212 may be structured differently, for example in deferent length, position within the airway adaptor 220, angle, number and position of sampling prongs and the like. The sampler 212 may include openings and/or funnel shaped collectors instead of one or more prongs and/or may include, for example one or more (for example 1, 2, 3 or more) prongs in each one of the sampling sides.

The moisture reduction system 202 may include a dryer tube which may include any drying mechanism and/or material that is capable of reducing the moisture level in the sampling system 200 and the sampling tubes. For example, the dryer tube may include Nafion® as referred to herein. In another example, the dryer tube may include filters such as microporous filters or molecular sieves (material containing tiny pores of a precise and uniform size that may be used to absorb moisture). The dryer tube may vary in length and/or in diameter. It is generally preferable that the dryer tube is adapted to absorb moisture and is essentially impermeable to gases. A filter of molecular sieve into which certain materials were impregnates may be included in the drying tube. The moisture reduction system 102 may also include a reinforcing element which is adapted to provide mechanical protection to the drying tube, for example prevent flow interruption, damaging, (partially) blocking, bending and/or collapsing of the drying tube. The reinforcing element may cover a portion of the drying tube. The reinforcing element may include, for example, a braiding net or any other form of mechanical support, such as rigid bars. The sampling tubing may further include another moisture reduction system (not shown), which may be the same or different from moisture reduction system 102 and a coupler that allows the connection of the sampling system 100 to a gas analyzer such as a capnograph (not shown).

The airway adapter 220 includes a deflector 230 located such that at least a part of the exhaled air flow (schematically shown by arrows 232) within the airway adapter 220 will encounter the deflector 230 prior to reaching the sampling inlet 210. As aforementioned, the sampling inlet 210 includes an opening 214 adapted to collect the sampled air. When liquid droplets or particles (such as 134), which may be present in an exhaled air flow, encounter the deflector they may be deflected from their initial course to a different towards the wall(s) 222 of the airway adapter 220 and thus the amount of liquids that reaches the sampling inlet 210 may be reduced.

The deflectors, such as deflector 230, may be positioned in front of the sampling input 212. These deflectors (obstacles) may be operative to deflect the heavier liquids toward the wall(s) 222 of the airway adapter 220. The liquids and secretions, which have relatively high inertia and which are flying toward the sampler 212, will be deflected to the sides, whereas the air (gas) current circumvents the obstacles and may enter the sampler 212 as required. Although FIGS. 3, 4a and 4b show a deflector 230 having three vanes, it is noted that any other appropriate deflector shape (such as but not limited to the examples provided herein) may be applied. For example, deflectors having 1, 2, 3, 4, 5 or more vanes may be applied.

The deflector 230 (or any other appropreate deflector) may be formed with and/or attached to a portion of the wall(s) 222 or the airway adapter 220.

The deflector 230 (or any other appropreate deflector) may refer to a molded-on deflector, which may be a part of (such as an integral part of) the airway adapter 220 (or any other appropreate airway adapter) and/or a separate element.

Deflecting the liquids that may be present in exhaled breath prior to their reaching the sampling inlet and thus preventing/reducing their entrance into the sampling tubes may solve or at least reduce the problem of damages caused by these liquids (for example, blocking and/or clogging the sampling tubing and input ports and damaging the analyzer).

According to some embodiments of the disclosure, one or more deflectors may be positioned such that the exhaled breath flow encounter the deflector(s) (such as deflector 230) prior to reaching the sampling inlet (such as sampling inlet 210). Preferably, the mechanism may be based on aerodynamic principles, such that the essentially laminar gas (breath) flow will be maintained.

For example, since liquids and secretions have higher inertia in comparison to the gas, the deflector(s) (such as deflector 230) may thus deflect the liquids and secretions away from the sampling inlet (such as sampling inlet 210) whereas the air circumvents the deflector(s) and enters the sampling inlet as required.

It is noted that other appropriate deflectors, connectors and/or adaptors, which may have different shapes and/or operative mechanisms, may be used.

Reference is now made to FIG. 5, which schematically illustrates exemplary cross section forms of a deflector such as a lens (convex, convex) (a); a tear drop (b); a diamond (c); a pear (d); an ellipsoid (e); an ovoid (f); an inverted ovoid (g) and a vane (H). Preferably, these shapes have rounded corners to prevent turbulent flow.

A "breath sampling inlet" as referred to herein may include an opening, aperture, orifice, valve or the like that is adapted for collection of fluid (such as breath exhale) from a subject's airway (such as an airway adaptor, airway tube or the like).

A "connector" as referred to herein may include any element that is adapted to bring two objects close to each other. A connector may refer to a molded-on connector, which may be a part of the drying mechanism and/or a separate element.

A "dryer mechanism" (or a drying mechanism) as referred to herein may include a dryer tube, a dryer sleeve that include material(s) capable of absorbing or passing moisture and/or humidity from a fluid such as exhaled breath. The dryer mechanism may have any other form, for example a sheet that allows reduction of humidity in sampled exhaled breath while maintaining the spacial resolution (and/or special integrity) of the collected breath samples. The dryer mechanism may includes for example, Nafion®. The dryer mechanism (such as the dryer tube) may include a reinforcing element.

For purposes of description, the discussion herein is focused on breath sampling, such as that of a human patient; however, it should be understood that the present disclosure is not limited in scope only for use with a patient and can beneficially be used in various other contexts.

While certain features of the disclosure have been illustrated and described herein, many modifications, substitutions, changes, and equivalents will now occur to those skilled in the art. It is, therefore, to be understood that the appended claims are intended to cover all such modifications and changes as fall within the true spirit of the disclosure.

What we claim is:

1. A breath sampling system comprising:
   a breath sampling tube and
   an airway adapter having an interior surface defining an inner channel with a first end, a second end and a longitudinal axis therebetween, said first end for connection to an endotracheal tube and said second end for connection to a ventilation tube, wherein said first end is configured to receive exhaled breath of a patient when in use; such that the exhaled breath flow from said first end to said second end of said inner channel; said airway adaptor comprising:
   a breath sampler extending through said interior surface of said adapter, such that an opening of said breath sampler is located within said inner channel, thereby enabling breath sampling by said breath sampler directly from said inner channel; and
   a deflector configured to deflect liquids, said deflector positioned within the inner channel of said adapter and separate from said breath sampler, such that a distance between said deflector and said first end along the longitudinal axis is smaller than a distance between said breath sampler and said first end along the longitudinal axis;
   wherein said deflector comprises one end which is narrower than a second opposing end, wherein the narrower end is located farther from said sampler than the second opposing end, thereby deflecting liquids away from said opening of said breath sampler and towards an interior surface of said airway adapter,
   wherein said deflector is aerodynamic such as to minimize laminar flow disruption thus facilitating the analysis of time dependent respiratory carbon dioxide ($CO_2$) concentration in exhaled breath by a capnograph.

2. The system according to claim 1, wherein said deflector comprises a hydrophobic material.

3. The breath sampling system of claim 1, wherein said breath sampler is perpendicular to airflow in said airway adapter.

4. An airway adapter comprising:
   an interior surface defining an inner channel having a first end, a second end and a longitudinal axis therebetween, said first end for connection to an endotracheal tube and said second end for connection to a ventilation tube; wherein said first end is configured to receive exhaled breath of a patient when in use, such that the exhaled breath flow from said first end to said second end of said inner channel;
   a breath sampler extending through said interior surface of said adapter, wherein said breath sampler protrudes into said channel, such that an opening of said breath sampler is located within said inner channel, thereby enabling breath sampling by said breath sampler directly from said inner channel; and
   a deflector configured to deflect liquids, said deflector positioned within the inner channel of said adapter and separate from said breath sampler, such that a distance between said deflector and said first end along the longitudinal axis is smaller than a distance between said breath sampler and said first end along the longitudinal axis; wherein said deflector comprises one end which is narrower than a second opposing end, wherein the narrower end is located farther from said sampler than the second opposing end, thereby deflecting liquids away from said opening of said breath sampler and towards the interior surface of said airway adapter;
   wherein said deflector is aerodynamic such as to minimize laminar flow disruption, thus facilitating the analysis of time dependent respiratory carbon dioxide ($CO_2$) concentration in a subject's breath by a capnograph.

5. The airway adapter according to claim 4, wherein said deflector comprises a hydrophobic material.

6. The airway adapter of claim 4, wherein said breath sampler is perpendicular to airflow in said airway adapter.

7. The airway adapter of claim 4, wherein said deflector does not contact said breath sampler.

8. The airway adapter of claim 4, wherein said deflector does not cover said opening of said breath sampler.

9. A breath sampling system comprising:
   a capnograph;
   a breath sampling tube, and an airway adapter configured to be connected to an endotracheal tube, said airway adapter comprising:
   an interior surface defining an inner channel with a first end, a second end and a longitudinal axis therebetween, said first end for connection to an endotracheal tube and said second end for connection to a ventilation tube, wherein said first end is configured to receive exhaled breath of a patient when in use, such that the exhaled breath flow from said first end to said second end of said inner channel;
   a breath sampler extending through said interior surface of said adapter, such that an opening of said breath sampler is located within said inner channel, thereby enabling breath sampling by said breath sampler directly from said inner channel; and a deflector adapted to deflect liquids, said deflector positioned within the inner channel of said adapter and separate from said breath sampler, such that a distance between said deflector and said first end along the longitudinal axis is smaller than a distance between said breath sampler and said first end along the longitudinal axis;
   wherein said deflector comprises one end which is narrower than a second opposing end, wherein the narrower end is located farther from said sampler than the second opposing end, thereby deflecting liquids away from said opening of said breath sampler and towards the interior surface of said airway adapter, wherein said deflector is aerodynamic such as to minimize laminar flow disruption, thus facilitating the analysis of time dependent respiratory carbon dioxide ($CO_2$) concentration in exhaled breath by said capnograph.

10. The system according to claim 9, wherein said deflector comprises a hydrophobic material.

11. The breath sampling system of claim 9, wherein said breath sampler is perpendicular to airflow in said airway adapter.

* * * * *